US005219482A

United States Patent [19]

Russo et al.

[11] Patent Number: 5,219,482

[45] Date of Patent: Jun. 15, 1993

[54] RUST AND HAZE INHIBITING LUBRICATING OIL ADDITIVE-REACTION PRODUCT OF N-ALKYL-MALIIMIDE AND 5-AMINO-TRIAZOLE

[75] Inventors: Joseph M. Russo, Poughkeepsie; Benjamin J. Kaufman, Hopewell Junction, both of N.Y.; Thomas F. DeRosa, Passaic, N.J.; Rodney L.-D. Sung, Fishkill, N.Y.

[73] Assignee: Texaco Inc., White Plains, N.Y.

[21] Appl. No.: 817,227

[22] Filed: Jan. 6, 1992

[51] Int. Cl.[5] .................. C10M 159/12; C07D 249/14

[52] U.S. Cl. .................................. 252/51.5 R; 252/51; 252/50; 252/51.5 A; 548/264.8

[58] Field of Search ....................... 252/51.5 R, 51, 50, 252/51.5 A; 548/264.8

[56] References Cited

U.S. PATENT DOCUMENTS

| | | | |
|---|---|---|---|
| 2,870,144 | 1/1959 | Schäfer et al. | 548/264.8 |
| 3,444,162 | 5/1969 | Hyatt | 548/264.8 |
| 3,483,211 | 12/1969 | Coburn | 548/264.8 |
| 4,615,970 | 10/1986 | Kojima et al. | 548/264.8 |
| 4,880,437 | 11/1989 | Karol | 44/341 |
| 4,963,278 | 10/1990 | Blain et al. | 252/51.5 A |
| 5,055,213 | 10/1991 | Germanaud et al. | 252/51.5 A |
| 5,059,336 | 10/1991 | Naka et al. | 252/51.5 A |
| 5,091,450 | 2/1992 | Borzatta et al. | 252/47.5 |
| 5,102,928 | 4/1992 | Borzatta | 252/51.5 R |

FOREIGN PATENT DOCUMENTS

| | | |
|---|---|---|
| 399834 | 11/1990 | European Pat. Off. . |
| 761456 | 9/1980 | U.S.S.R. . |

*Primary Examiner*—Prince Willis, Jr.
*Assistant Examiner*—James Silbermann
*Attorney, Agent, or Firm*—James J. O'Loughlin; Christopher Nicastri

[57] ABSTRACT

A lubricating oil additive with rust and haze inhibiting properties which comprises the reaction product of a long chain alkyl substituted maleimide represented by the figure

O
N—R
O where R is $C_3$–$C_{30}$ alkyl radical comprising and 5-amino-triazole is provided. A lubricating oil composition containing the additive is also provided.

10 Claims, No Drawings

RUST AND HAZE INHIBITING LUBRICATING OIL ADDITIVE-REACTION PRODUCT OF N-ALKYL-MALIIMIDE AND 5-AMINO-TRIAZOLE

BACKGROUND OF THE INVENTION

1. Field of the Invention

This invention relates to an additive which imparts haze-free rust inhibition to diesel lubricating oils, and to a diesel lubricating oil composition which contains such an additive. More specifically, this invention relates to a diesel lubricating oil additive which comprises the reaction product of a maleimide and an amino-triazole, and to a diesel lubricating oil composition in which the additive of the present invention is dissolved.

2. Description of Related Information

As is well known to those skilled in the art, lubricating oils must be characterized by resistance to oxidation, and by rust and corrosion inhibition. It is also desirable from aesthetic perspective to have a haze-free product. The oils used as lubricants in the crankcases of large diesel engines, such as marine and railway diesel engines, are subject to uniquely harsh operating conditions and thus special attention must be directed to the severe problems which are encountered. These oils are therefore typically formulated to contain anti-wear additives, oxidation inhibitors, demulsifying agents, rust-inhibitors, etc.

Lubricants used in the crankcases of marine diesel engines are burdened by a severe rust protection requirement. The rust forms as the result of water coming into contact with ferrous metal engine parts. There are two water sources which are responsible: the first is water produced by the combustion of the diesel fuel; the second is seawater. Of the two, seawater is considerably more abundant and corrosive.

This is an old problem, and diesel lubricating oils have been formulated with additives to inhibit the formation of rust. However, the treatment of one problem, i.e., rust formation, has introduced another problem. The addition of rust inhibitors to lubricating oil compositions has been found to cause the formation of haze in the lubricating oil. The formation of haze is undesirable since it masks or interferes with the determination of the presence of undesirable components, including decomposition products, water, and solid particles in the lubricant.

In addition, consumers have come to equate product clarity or aesthetics with product superiority. In this context, hazy products would dramatically curtail product acceptance by consumers.

The advent of new, more fuel efficient railway diesel engines has put a greater demand on the oxidation resistance of railway diesel lubricants. Oxidized lubricants lead to increased corrosive attack of engine metal surfaces; consequently, lubricants employed in newer railway diesel engines must be changed more frequently to prevent such corrosive attack.

Thus, there is a need for an additive which will impart rust inhibition to diesel lubricating oil compositions, but which does not cause haze to form.

It is an object of this invention to provide a diesel lubricant additive which will inhibit the formation of rust in a lubricating oil, but which will not cause undesirable haze to form. It is another object to provide a novel lubricant composition, suitable for use in large marine and railway diesel engines, characterized by its rust and haze resistance. It is still a another object of this invention to provide a process for producing such a lubricating oil additive and a method for imparting rust resistance to a lubricating oil without causing haze to form. Other objects will be apparent to those skilled in the art.

SUMMARY OF THE INVENTION

The present invention provides: a diesel lubricating oil additive which imparts rust and haze inhibition to diesel lubricating oil compositions and diesel lubricating oil compositions containing such additives.

The diesel lubricating oil additive of the present invention comprises the reaction product of a maleimide (I) represented by the general formula:

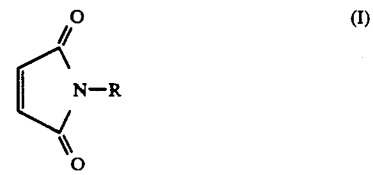

(I)

where R is an alkyl radical containing about 3 to about 30 carbon atoms; and an amino-triazole (II) represented by the formula:

(II)

$H_2N$ — N — NH — N (amino-triazole structure)

The diesel lubricating oil additive of the present invention is the addition product of the two aforementioned components (III):

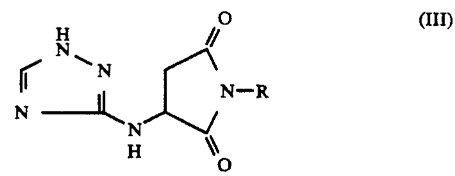

(III)

The present invention also provides a diesel lubricating oil composition comprising a major portion of a hydrocarbon lubricating oil and a minor, effective portion of the additive composition described above, sufficient to impart rust inhibition and haze resistance to the diesel lubricating oil composition.

DETAILED DESCRIPTION OF THE INVENTION

The Maleimide Reactant

The maleimide reactant is represented by the general formula:

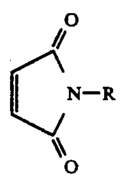

where R is an alkyl radical containing about 3 to about 30 carbon atoms. Preferably R contains about 3 to about 15 carbon atoms. R may be aliphatic, cyclic or acyclic, branched in a systematic or random fashion or unbranched; aromatic-aliphatic; aliphatic-aromatic; aromatic with one or more substituents on the aromatic ring; or polyaromatic. Moreover, R may contain one or more heteroatoms, e.g., nitrogen and oxygen.

The maleimides useful in the practice of the present invention can be produced by imidizing maleic anhydride with a long chain aliphatic primary amine according to the reaction depicted in the following equation:

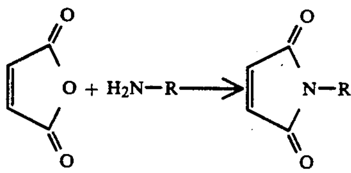

where R is defined as above.

The Amino-Triazole Reactant

The amino-triazole reactant useful in this invention is represented by the formula:

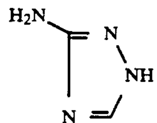

Long chain polyaliphatic amines are available from Texaco Chemical Company, Austin, Tex.; maleic anhydride is available from Allied Chemical Company, Morristown, N.J.; and amino-triazole is available from Aldrich Chemical Company, Milwaukee, Wis.

The additive of the present invention is produced by reacting equivalent amounts of the aliphatic maleimide with the amino-triazole according to the reaction depicted in Equation 1:

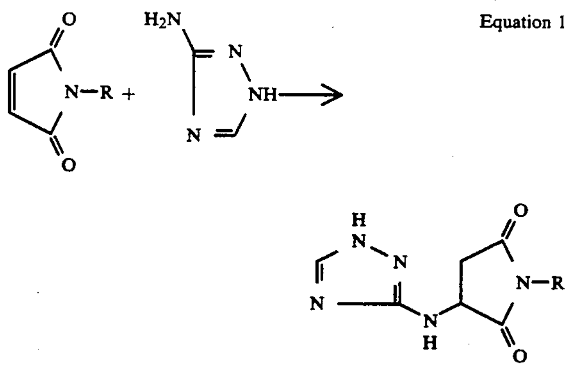

The following examples are provided to illustrate the synthesis of key components of this invention.

EXAMPLE 1

Preparation of N-(n-nonyl)-maleimide

One equivalent each of maleic anhydride and n-nonylamine are charged into a 1 liter 3-neck round bottom glass flask containing 300 ml xylene, a reflux condenser with a Dean-Stark attachment, Teflon-coated magnetic stirring bar, and a thermometer. The contents are heated to 120° C. for about 15 hours, the reaction extent being monitored by the amount of water collected. After 1 equivalent of water is collected, the reaction solvent is flash distilled off. The absence of an infrared absorbance at 1830 $cm^{-1}$ and 1791 $cm^{-1}$ is evidence of anhydride consumption; the presence of an infrared absorbance at 1772 $cm^{-1}$ is evidence of imide formation.

EXAMPLE 2

Preparation of N-(octyl)-maleimide n-Octylamine may be substituted in Example 1.

EXAMPLE 3

Preparation of N-(tetracosane)-maleimide n-Tetracosylamine may be substituted in Example 1.

EXAMPLE 4

Preparation of [3-(1,2,4-triazole)]-[N-(n-nonyl)-succinimide]-amine

One equivalent each of N-(n-nonyl)-maleimide and 3-amino-1,2,4-triazole were charged into a 1 liter 3-neck round bottom flask containing 300 ml xylene. The mixture was heated to 155° C., i.e., reflux temperature, for 6 hours. The solvent was flash distilled over and a brownish solid was isolated. The absence of an olefinic absorbing band at 1610 $cm^{-1}$ was evidence of a successful addition.

EXAMPLE 5

Preparation of [1,2,4-triazole)]-[N-(n-octyl)-succinimide]-amine

N-(n-octyl)-maleimide may be substituted in Example 5.

The lubricating oil compositions of the present invention may be made by any procedure for making lubricating oil compositions. Typically, the additive is added to the lubricant by simply mixing the components together, producing a lubricant with increased oxidation and corrosion resistance.

The lubricating oil component of the lubricating oil compositions can typically include one or any combination of the following: hydrocarbon oils, such as those having naphthenic base, paraffinic base, mixed base mineral oils; oils derived from coal products; synthetic oils, such as alkylene polymers including polypropylene and polyisobutylene having molecular weights of between about 250 and 2500; and the like. The type of lubricant can vary depending upon the particular application or properties desired. For example, marine diesel engine lubricants can contain hydrocarbon lubricating oil having a Total Base Number (TBN) of 3–8, typically 6, which may be made by blending paraffinic Solvent Neutral Oil (SNO)-20 having a Viscosity Index (VI) of about 92 and a viscosity of 47–53 centistokes (CSt.) at 40° C. and of 6.65–7.15 CSt. at 100° C., with a paraffinic SNO-50 having a VI of about 93 and a viscosity of 158–180 CSt at 40° C. and of 15.3–16.4 at 100° C. Typical railway diesel engine lubricants can contain mixtures of paraffinic mineral oil having a viscosity of 5.5–10.0, such as 8.5 CSt at 100° C., paraffinic mineral oil having a viscosity of 8.0–15.0, such as 14.5 CSt at 100° C., and naphthenic pale oil having a viscosity of 8.0–15.0, such as 14.2 CSt at 100° C. Preferred lubricants include: N300 Pale Oil from Texaco Inc.; N900 Pale Oil from Texaco Inc.; and the like.

The additive of the present invention may be added to the base lubricating oil in any minor, effective, rust and haze inhibiting amounts. Preferably the additive will be added to the base lubricating oil in amounts of about 0.1 to about 5 wt. % based on the weight of the lubricating oil. More preferably the effective amount is about 1 wt. % to about 3 wt. %, based upon the weight of the lubricating oil. The additive mixture may be added separately, or as a component of an additive package which contains other additives.

The lubricant composition can contain, if desired, any other materials useful in lubricants. Such other materials include, among others, one or more of the following: dispersants; detergents; viscosity index improvers; antifoamants; antiwear agents; demulsifiers; other anti-oxidants; other corrosion inhibitors; and other materials useful in lubricants. Preferred optional additives or additive packages include: ORONITE® 2939 from Chevron Chemical Company; polymethylmethacrylate, a pour point depressant available from Rohm & Haas, Philadelphia, PA. and the like. The amount of such materials may be any desired amounts which provide the desired properties.

The additive of the present invention is advantageous in that it imparts rust inhibition to diesel lubricating oil compositions without causing haze to form. These advantages are illustrated by the comparison of Examples A–C, listed in Table II. Example A is commercially available Doro AR®, a slow speed marine crankcase formulation available from Deutsche Texaco Additive. Example B is the same lubricant, Doro AR®, with the commercial rust inhibitor, Surfonic N-60 TM, removed. Example C is Doro AR® with the commercial rust inhibitor removed and the additive of Example 4 substituted in its place.

TABLE II

| Material | Example A | Example B | Example C |
|---|---|---|---|
| SNO-20G DTA | 39.30 | 39.30 | 39.30 |
| SNO-50 DTA | 55.80 | 56.15 | 55.15 |
| detergent | 3.60 | 3.60 | 3.60 |
| anti-wear agent[4] | 0.65 | 0.65 | 0.65 |
| anti-oxidant[2] | 0.30 | 0.30 | 0.30 |
| anti-foam agent[5] (ppm) | 150 | 150 | 150 |
| anti-rust agent[3] | 0.35 | — | — |
| Experimental Additive of Example 4 | — | — | 1.0 |

[1]Oronite 218A brand of overbased sulfurized calcium alkylphenolate having a TBN of 147, available from the Chevron Oil Company.
[2]Vanlube NA brand of dinonyl phenyl amine, available from RT Vanderbilt, of Norwalk, Ct.
[3]Surfonic N-60, available from the Texaco Chemical Company, Houston, Texas.
[4]Zinc di-thiophosphate
[5]TX-1416 brand of anit-foam agent, available from the Texaco Chemical Company.

The lubricating oil compositions of Examples A, B and C were subjected to the ASTM D-665 Saltwater Test to determine the level of rust inhibition.

ASTM D-655 Saltwater Test

This test method is used to evaluate the ability of inhibited mineral oils to aid in preventing the rusting of ferrous parts should water become mixed with the oil.

A mixture of 300 ml of the oil under test is stirred with 30 ml of synthetic sea water as required, at a temperature of 60° C. (140° F) with a cylindrical steel specimen completely immersed therein. The test is run for 24 hours. The specimen is observed for signs of rusting and, if desired, the degree of rusting.

In addition, each composition was tested with the Hazitron TM, an instrument which measures haze.

Hazitron test Method

This method is intended for the determination of the clarity of petroleum products such as lubricating oils and their additives. The Hazitron instrument rates clarity essentially as perceived by the human eye.

The Hazitron measures light scattering caused by haze. The method is based on measurements of transmitted light through the sample placed in two positions of the sample compartment.

Clarity is an important characteristic of lubricating oils and their additives. A method using the Hazitron allows one to evaluate clarity objectively.

Hazitron values of 15 or less indicate commercially acceptable product clarity. The results of the ASTM D-665 Saltwater Test and the Hazitron test are summarized in Table III.

TABLE III

| | Example A | Example B | Example C |
|---|---|---|---|
| Hazitron Turbidity | 55 | 9 | 8 |
| ASTM Salt Water Test | Pass | Fail | Pass |

The results of these tests clearly show that the additive of the present invention provides marine crankcase lubricants with rust inhibition which is at least as effective as the commercially used rust inhibitor. In addition, it is clear that the commercial rust inhibitor causes haze to form in the lubricant. On the other hand, the additive of the present invention decreases haze in the lubricating oil composition.

Thus, the additive of the present invention effectively imparts rust inhibition and haze resistance to lubricating oil compositions.

We claim:

1. A lubricating oil additive which comprises the reaction product of a maleimide represented by the formula

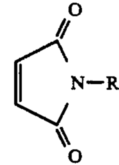

where R is an alkyl radical containing about 3 to about 30 carbon atoms and an amino-triazole represented by the formula

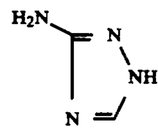

2. The lubricating oil additive of claim 1 where R is an alkyl radical containing about 3 to about 15 carbon atoms.

3. The lubricating oil additive of claim 1 where about 1 mole of the maleimide is reacted with about 1 mole of the triazole.

4. A lubricating oil additive comprising the compound represented by the formula

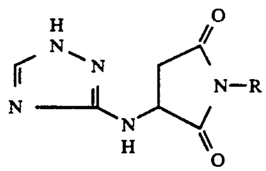

where R is an alkyl radical containing about 3 to about 30 carbon atoms.

5. The lubricating oil additive of claim 4 where R is an alkyl radical containing about 3 to about 15 carbon atoms.

6. A lubricating oil composition comprising a major portion of a base hydrocarbon lubricating oil and a minor portion, sufficient to impart rust and haze inhibition to the lubricating oil composition, of a lubricating oil additive comprising the reaction product of a maleimide represented by the formula

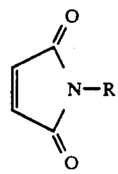

where R is an alkyl radical containing about 3 to about 30 carbon atoms and an amino-triazole represented by the formula

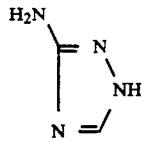

7. The lubricating oil composition of claim 6 where R is an alkyl radical containing about 3 to about 15 carbon atoms.

8. The lubricating oil additive of claim 6 where about 1 mole of the maleimide are reacted with 1 moles of the triazole.

9. The lubricating oil composition of claim 6 where the lubricating oil additive comprises the compound represented by the formula

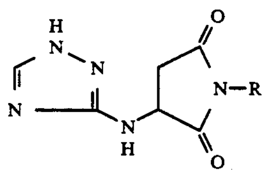

where R is an alkyl radical containing about 3 to about 30 carbon atoms.

10. The lubricating oil composition of claim 9 where R is an alkyl radical containing about 3 to about 15 carbon atoms.

* * * * *